United States Patent
Guterstam et al.

(10) Patent No.: US 11,549,143 B2
(45) Date of Patent: Jan. 10, 2023

(54) COMPOSITIONS FOR USE IN SECURITY MARKING

(71) Applicant: Selectamark Security Systems PLC, Locksbottom (GB)

(72) Inventors: Peter Guterstam, Vasteras (SE); James Brown, Locksbottom (GB)

(73) Assignee: Selectamark Security Systems PLC, Locksbottom (GB)

( * ) Notice: Subject to any disclaimer, the term of this patent is extended or adjusted under 35 U.S.C. 154(b) by 398 days.

(21) Appl. No.: 15/578,027

(22) PCT Filed: May 27, 2016

(86) PCT No.: PCT/EP2016/062051
§ 371 (c)(1),
(2) Date: Nov. 29, 2017

(87) PCT Pub. No.: WO2016/193164
PCT Pub. Date: Dec. 8, 2016

(65) Prior Publication Data
US 2018/0291446 A1    Oct. 11, 2018

(30) Foreign Application Priority Data

May 29, 2015   (GB) ..................... 1509308

(51) Int. Cl.
*C12Q 1/68* (2018.01)
*C12Q 1/6876* (2018.01)
*G08B 15/02* (2006.01)
*C12Q 1/6813* (2018.01)

(52) U.S. Cl.
CPC ......... *C12Q 1/6876* (2013.01); *C12Q 1/6813* (2013.01); *G08B 15/02* (2013.01)

(58) Field of Classification Search
CPC .... C12Q 1/6876; C12Q 1/6813; G08B 15/02; G08B 25/01; G08B 25/014
See application file for complete search history.

(56) References Cited

U.S. PATENT DOCUMENTS

| | | | |
|---|---|---|---|
| 9,919,512 B2 * | 3/2018 | Jung | C12Q 1/68 |
| 2003/0235836 A1 | 12/2003 | Simonetta et al. | |
| 2005/0214532 A1 * | 9/2005 | Kosak | D06M 15/01 |
| | | | 428/364 |
| 2014/0150708 A1 * | 6/2014 | Riekie | G08B 15/02 |
| | | | 116/201 |

FOREIGN PATENT DOCUMENTS

| | | | | |
|---|---|---|---|---|
| WO | 94/04918 A1 | 3/1994 | | |
| WO | 95/02702 A1 | 1/1995 | | |
| WO | 02/093504 A2 | 11/2002 | | |
| WO | 03/074733 A1 | 9/2003 | | |
| WO | WO-03074733 A2 * | 9/2003 | ....... | C12Q 2537/143 |
| WO | 2009/112507 A1 | 9/2009 | | |
| WO | 2010/122159 A1 | 10/2010 | | |

OTHER PUBLICATIONS

Humenik et al. (J Phys Condens. Matter, 2014, 26, 503102, p. 1-12) (Year: 2014).*
Isgrove, Andrew, GB Search Report, Great Britain Intellectual Property Office, GB1509308.1, dated Nov. 20, 2015.
Mueller, Frank, International Search Report and Written Opinion, PCT/EP2016/062051, European Patent Office, dated Aug. 26, 2016.

* cited by examiner

Primary Examiner — Stephanie K Mummert

(57) ABSTRACT

Provided is a security marking composition for marking an area of land, which security marking composition is readily capable of transfer from the land to a person or to a vehicle, which security marking composition comprises:
  (a) a carrier selected from a polymer and an emulsion; and
  (b) a security marker.

15 Claims, 5 Drawing Sheets

COMPOSITIONS FOR USE IN SECURITY MARKING

CROSS REFERENCE TO RELATED APPLICATIONS

This application is a U.S. National Stage Application filed under 35 U.S.C. § 371 and claims priority to International Application No. PCT/EP2016/062051, filed May 27, 2016, which application claims priority to Great Britain Application No. 1509308.1, filed May 29, 2015, the disclosures of which are incorporated herein by reference.

FIELD OF THE INVENTION

The present invention relates to security compositions suitable for the security marking of an area of land, and methods of manufacturing said compositions. The compositions may comprise synthetic nucleotide security marker. The invention also relates to the use of the compositions in security marking of an area of land, or of property, and/or for marking a poacher, thief, attacker, or other person, and methods of detecting such a composition, in particular on a person, a vehicle, or property. The invention also extends to methods of analysing the composition to determine the origin of the composition and/or information about the owner of the land or property.

BACKGROUND OF THE INVENTION

Synthetic nucleotide containing compositions for use in security marking of property and/or for marking a thief or attacker are known in the art. Indeed, the present applicant has already developed and marketed several products containing such compositions. Some examples of the present applicant's products which utilize such compositions are discussed below.

The SelectaDNA® property marking kit comprises a pot of adhesive which can be applied to property using an applicator in order to mark the property with a unique composition which can be traced back to the owner in the event of the property being stolen by a thief and then retrieved by the police. Each pot of adhesive contains a unique DNA composition and also several thousand microdots dispersed throughout the adhesive. Each microdot contains a unique registration code and a database telephone number or internet address. A database is maintained by a service provider linking each unique registration code to details of the owner of the property, e.g. name, address and/or telephone number of the owner. These details may be obtained when an owner of the property purchases the property marking kit and entered into the database. This database, or a second database, also contains information about the unique DNA composition which is either linked to the registration code or directly to the owner's details. The adhesive also contains a fluorescent material which emits visible light under UV light in order to allow the adhesive marking on the property to be readily located by the police.

The aforementioned kit provides two possible methods for tracing the owner of stolen property, via the microdots or via the unique DNA composition. However, for some applications it may not be appropriate to provide microdots in a security marking composition. For example, it may not be appropriate to provide microdots in compositions which are to be expelled as an aerosol to mark a thief or attacker as such microdots may block the dispensing nozzle and/or be readily washed off.

Such is the case for the present applicant's DNA personal alarm which does not use microdots. This product comprises a hand-held personal alarm in the form of a pressurized container housing a composition which comprises a unique DNA composition and a fluorescent material of the kind used in the previously described property marking kit. As described in relation to the property marking kit, a database is maintained by a service provider linking information about each unique DNA composition to details of the owners of the personal alarms. If an owner is attacked they can spray their attacker using the personal alarm. Subsequently, if apprehended, a UV lamp can be utilized to locate the DNA composition on the attacker. A small sample of the composition can be removed and sent to a laboratory for analysis to obtain information about the unique DNA composition. This information can then be used to identify the owner of the personal alarm using the database. As such, the attacker can be unarguably linked to the attack on the owner of the personal alarm, any stolen property can be returned, and the information used to secure a conviction.

Yet another use of synthetic DNA containing compositions is in building security system, particularly at entry points such as doors and windows. A building security system which dispenses a fluid for deterring and/or identifying an intruder is described in the present applicant's own earlier patent application, WO 2009/112507. In this earlier application it is described that a particularly useful formulation comprises a DNA marker/identifier, a UV tracer/fluorescent material, a propellant, and optionally a solvent which may be organic, e.g. an alcohol, or aqueous. As with the aforementioned property marking kit and personal alarm, a database is maintained by a service provider linking information about each unique DNA composition to details of the owners of the security system. If a building is broken into by a burglar, the security system sprays the intruder with the DNA composition. Subsequently, if apprehended, a UV lamp can be utilized to locate the DNA composition on the intruder. A small sample of the composition can be removed and sent to a laboratory for analysis to obtain information about the unique DNA composition. This information can then be used to identify the owner of the building using the database. As such, the intruder can be unarguably linked to the burglary such that any stolen property can be returned and the information used to secure a conviction.

The synthetic DNA compositions used in these products were not originally optimized for the security marking applications described. The present applicant developed improved DNA tags for use in security marking, as described in WO 2010/122159. Further improvements, for example in delivery mechanisms have also been made by the present applicant, such as described in WO 2013/171279.

Despite these improvements in security tagging technology, these systems are particularly suited to marking property, or marking people, such as rioters, or intruders who break into a building. None of these systems are particularly suited to marking areas of land. This is unfortunate, because there is a growing demand for security marking land areas, not only to deter trespassing onto private or commercial property, but also to deter poaching, illegal dumping, illegal mining and the like. These applications are typically required in more remote places, sometimes over a large land area. The current systems are not adapted for such wide coverage, nor are they well adapted to transfer a security marker, such as DNA, from land or vegetation to a person or vehicle that is intruding. Furthermore, within the context of marking land, there is a need for monitoring animal movement (e.g. cattle or protected species) and current systems are also not suited to this.

Some security marking systems have been developed to facilitate transfer of a security marker from property to a person. For example, GB 2,390,055 discloses a marking apparatus which, on activation, releases a marking fluid onto bank notes, which fluid is in turn transferred to a person. The marking fluid may comprise DNA. However, this system, like the others described above, is not suited to marking areas of land, nor is it suited for transferring a security marker from land or vegetation to a person or vehicle.

It is an aim of the present invention to solve the problems associated with the known systems described above. In particular, it is an aim of the present invention to provide security compositions suitable for the security marking of an area of land, and methods of manufacturing said compositions. It is also an aim to provide uses of the compositions in security marking of an area of land, or an area of property, and/or for marking a poacher, thief, attacker, or other person, and methods of detecting such a composition, in particular on a person, a vehicle, or property. It is a further aim to provide methods of analysing the composition to determine the origin of the composition and/or information about the owner of the land or property.

SUMMARY OF THE INVENTION

The present invention provides a security marking composition for marking an area of land, which security marking composition is readily capable of transfer from the land to a person or to a vehicle, which security marking composition comprises:

(a) a carrier selected from a polymer and an emulsion; and
(b) a security marker.

In the present context an area of land is not especially limited, and may comprise any land. Typically the land may be outdoors, and may comprise earth and/or rock and/or vegetation (such as grass, shrubs, trees and the like). The land may also comprise stretches of water, such as a river, a lake or a stream. The land may further comprise an indoor area, such as an area of property, for example indoor passageways, doorways, or openings, and the like, through which people, animals or vehicles may pass.

Irrespective of whether the land is outdoors or indoors, it is particularly preferred that it comprises an area through which animals, people or vehicles are likely to pass. Thus, as has been mentioned, when indoors it may include passageways and doorways, but when outdoors may include gateways, paths, roads, thoroughfares, field entrances and the like.

The transfer of the composition from the land to a person is required in order for the security marker to be detected. However, the transfer is not especially limited. In the present context a composition is readily capable of transfer if the security marker is transferable in sufficient quantity to be subsequently detected. Transfer to a person may be to skin or clothes, whilst transfer to a vehicle may be to the body of the vehicle, or more typically to tyres.

The carrier is not especially limited, provided that it is capable of holding sufficient quantity of security marker to be subsequently detected, and provided that the carrier is capable of transferring at least that quantity from the land to a person or to a vehicle. The carrier is typically a sticky carrier. In this context, sticky means capable of adhering to land such that it does not disperse significantly away from the area of application, but also capable of transferring from the land to a person or to a vehicle. In some embodiments, the polymer carrier is in the form of a thread, especially a fine thread, similar to a spider-web or fishing line. In other embodiments the carrier may be in the form of small spheres or balls.

Thus, typically the polymer is a sticky polymer. Suitable sticky polymers should also be either absorbent or adsorbent enough to carry sufficient quantity of security marker. Typical such sticky polymers may be formed from a polyacrylamide or a synthetic spider silk protein, or a polymer capable of being formed into a thread. Adhesive may be added to the composition to increase stickiness, if desired, but this is optional rather than essential since some polymers (e.g. spider silk) and some emulsions (e.g. oil and water emulsion) are sufficiently sticky without adhesive.

Polyacrylamide in the form of small spheres (e.g. microspheres) or balls is a preferred carrier in the present invention. The spherical form is particularly suited for transferring from land to a person or vehicle by adhering to shoes or tyres. The polymer is known in a variety of consumer products for its ability to absorb water up to several hundred times its own mass. Polyacrylamide is also used in agricultural applications, e.g. as soil conditioner, or even as land filling. It is also used by the construction industry, for example to seal tunnels from water permeation. Accordingly, this carrier has all of the necessary properties for the current application.

By exposing dry polyacrylamide balls to the applicant's liquid products comprising the security marker (such as the SelectaDNA spray) wet balls are generated that readily transfer SelectaDNA and optionally a UV-brightener or alternative marker upon contact.

The polyacrylamide balls are particularly effective when dispersed on solid ground, since they will be deformed or burst and stick to the sole of a shoe or tyre when being stepped on or driven over. The applicant has determined that shoes remain tagged several weeks after contact with the present composition, and car tyres and surrounding wheel arches remain tagged even after having been driven for dozens of miles. The polyacrylamide balls also enable secondary transfer, for example resulting in transfer from shoes to car accelerator pedals. This tagging has been shown to remain for months after contact with a tagged shoe sole. It has also been observed that the undercarriage of a car remains tagged several months after the car has driven over the polyacrylamide balls.

Spider silk (or synthetic spider silk protein) in the form of threads is an alternative preferred carrier in the present invention. This form is particularly suited for transferring from more open areas where the balls are not suitable, or by open water, such as by a stream or lake. The security marker may be applied by using thin threads soaked in the security marker. Preferably the threads are soaked in a sticky liquid, such as the emulsion described below. The threads are typically very thin, and so (despite being strong) they will break easily if someone is passing. The threads then stick to skin and clothing.

Synthetic spider silk protein thread is produced commercially and is available on the market. However, currently, it is still expensive, and may typically be more suitable for high profile crime investigations, when invisibility is crucial. For other applications, for example tagging illegal trespassers in nature reserves, there are less expensive alternatives, which are suitable for use in the present invention, which comprise other polymer carriers in the form of a thread, especially a fine thread. Thus, a more affordable thread is so-called "spider web thread", which is a commercially available thread developed for e.g. fly fishing applications. This thread is also very fine and it is also advantageous since the material, usually cotton, absorbs water, and thereby the security marker, very well.

As a still further alternative, fine nets similar to spider-web, but which are currently used for gardening applications, may also be useful as a carrier.

As has been mentioned, an emulsion (especially a sticky emulsion) is also suitable as a carrier in the present invention. The emulsion comprises a water-based component and a hydrophobic liquid component (such as an oil). The emulsion may be used as a carrier on its own, or may be used to stick to the surface of another carrier, such as the threads described above. This latter application is particularly preferred for carriers which are not absorbent, and which are not suitable for carrying the security marker on their own.

One preferred sticky emulsion comprises a mixture of oil and water. This emulsion comprises a frothy, greasy and slightly sticky liquid (similar to French vinaigrette) that is particularly suitable for application to vegetation. This particularly applies in shrubby areas (such as areas comprising small bushes, shrubs and/or undergrowth). The sticky liquid is particularly suitable for transfer to skin and clothes if a person comes into contact with such shrubbery. The oily emulsion not only enhances the likelihood of successful transfer of security marker to potential trespassers, but also limits evaporation as compared with a simple water solution. This is particularly useful in warm climates, since it enhances the longevity of effective protection by limiting evaporation. The sticky liquid is complementary to the polymer carrier, whether in ball or thread form, since it is typically applied in areas where practical circumstances (like the terrain or vegetation) limit effective use of polymer spheres or threads.

Once distributed, the sticky emulsion will be retained on leaves, needles, grass and other vegetation in the marked land area, and direct contact will lead to transfer of the sticky liquid and thus the security marker.

The security marker used in the present application is not especially limited, provided that it is capable of uniquely marking the land area. Any security marker may thus be employed, provided that it remains intact and detectable in the environment in which it is employed. Examples of such markers include standard markers used in security marking, such as UV, IR and light activated luminescent compounds, or electromagnetically active identifiers. For example, blue UV-activated dye may typically be employed. A further such security marker may comprise nucleic acid, such as DNA. Methods for employing DNA in the present invention will be described by way of example herein, but it will be apparent that the other markers described herein may alternatively (or additionally) be employed as required.

Typically, when the security marker employs DNA, it comprises: a plurality of identical first synthetic nucleotide oligomers; and a plurality of identical second synthetic nucleotide oligomers which are different to the first synthetic nucleotide oligomers, wherein each of the first synthetic nucleotide oligomers comprises a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers comprises a third primer binding sequence of bases, a second identifier sequence of three to seven bases in length, and a fourth primer binding sequence of bases, the second identifier sequence being disposed between the third and fourth primer binding sequences, and wherein the first identifier sequence is different to the second identifier sequence.

The oligomers are constructed so that they can easily be related to the owner of the composition, using a database. Thus the first and second identifier sequences are relatable to the owner of the composition via a database. The database contains information on the owner of the composition and connects this information to the first and second identifier sequences. Thus the information on the owner can be obtained from identification of the first and second identifier sequences in the composition.

Compositions according to embodiments of the present invention may comprise further components as described in the background section. For example, compositions may comprise microdots, fluorescent material, adhesive, grease, gel, an organic or aqueous solvent, and/or a propellant. According to one embodiment, the composition comprises an adhesive in which the oligomers are dispersed. According to another embodiment the composition comprises a solvent which renders the composition sprayable. According to this embodiment, a pressurized container may be provided to house the composition, the container comprising a nozzle for spraying the composition. According to other embodiments, the composition comprises a grease or gel in which the oligomers are dispersed.

According to certain embodiments, the composition may further comprise a plurality of particles or molecules which provide an optical signature. For example, the plurality of particles or molecules may provide a range of refractive properties which can be scanned and used to identify the composition. According to embodiments, nanoparticle such an inorganic ceramic powder may be dispersed in the composition. A range of different powders provide a range of distinct optical signatures which can be used to identify the composition. The range of unique optical signatures will generally be less than the range of different nucleotide sequences. As such, the optical signature may not uniquely label every different composition in practice. However, such an optical signature can be useful to identify a manufacturer of the compositions, a supplier, a source and/or batch of compositions.

In light of the above, it is evident that compositions according to embodiments of the present invention may provide a cascading range of different identification components and methods. At a top level, the composition may have a specific colour, e.g. a blue colour under fluorescent light or a green colour under infra-red light. This may serve to identify a company using that colour. However, as more companies enter this field, it is likely that certain companies will end up using the same fluorescent colour for their identifier compositions. A second level of identification may be provided by way of microdots identifying the source of the compositions more precisely. However, if a sample of the composition does not contain a microdot then some other means is required to identify the source of the composition. A third level of identification may thus be provided by way of an optical signature using a plurality of optically active molecules or nanoparticles dispersed in the composition to identify the source of the composition. Finally, a fourth level of identification is provided by way of the nucleotide identifier sequences to precisely and uniquely identify each and every individual composition. Such a cascading range of identification methods provides a range of different levels of identification so as to ensure that identification will be successful. Furthermore, top level identification is made quick and cheap to perform without overly complex or expensive equipment allowing individuals or police forces to identify a central source for a composition. The more complex and time consuming nucleotide analysis can thus be centralized.

The compositions will generally be manufactured by forming the nucleotide oligomers and then dispersing them in the polymer or emulsion carrier. The polymer or emulsion carrier may itself be formed into a suitable medium for deployment, e.g. as an adhesive, grease, gel or spray. The compositions will then be loaded into suitably coded containers and a record made to link each coded container to its nucleotide code. When sold to a customer, details of the custom are taken along with the code of the purchased container. Thus, the customer's details can be tied to the nucleotide code in a database as described in the background section.

According to embodiments of the present invention, security marking or tagging technology may comprise (but not limited to) nucleotide oligomers, which may comprise DNA or RNA. DNA is preferred as it is more stable. The nucleotide oligomers may be single stranded or double stranded.

According to another aspect of the present invention a plurality of containers of the composition are provided. Each container is identifiable by a unique combination of the first and second identifier sequences. The containers may be grouped in batches, wherein the first identifier is for identifying the batch to which a container belongs and the second identifier is for uniquely identifying each container within said batch.

The present invention further provides a security marking kit is provided, the kit comprising:

(1a) a security marking composition as defined above; and/or (1b) a pressurized container a pressurized container as defined above; and (2) instructions for recording ownership of the kit in a database.

According to another aspect of the present invention, the composition is used in security marking of land, and/or property and/or for marking a poacher, a thief or an attacker.

According to another aspect of the present invention, there is provided a method of determining an owner of a composition as described herein, the method comprising: taking a sample of the composition; reacting one or both of the first and second synthetic nucleotide oligomers with primers which bind to the first and second and/or third and fourth primer binding sequences to increase the length of one or both of the first and second synthetic nucleotide oligomers; amplifying one or both of the first and second synthetic nucleotide oligomers using a polymerase chain reaction; sequencing the amplified synthetic nucleotide oligomers to identify the first and/or second identifier sequence; and consulting a database to match the identified first and/or second identifier sequence with information about the owner of the composition.

The primers may comprise primer sequences which are standard primer sequences used in Sanger amplification and sequencing. The primers are longer than the primer binding sequences in order to improve sequencing accuracy. For example, the primers may have a length in the range 50 to 200 bases, preferably 50 to 100 bases.

BRIEF DESCRIPTION OF THE DRAWINGS

For a better understanding of the present invention and to show how the same may be carried into effect, embodiments of the present invention will now be described by way of example only with reference to the accompanying drawings, in which.

DETAILED DESCRIPTION OF THE PREFERRED EMBODIMENTS OF THE INVENTION

Figure 1:
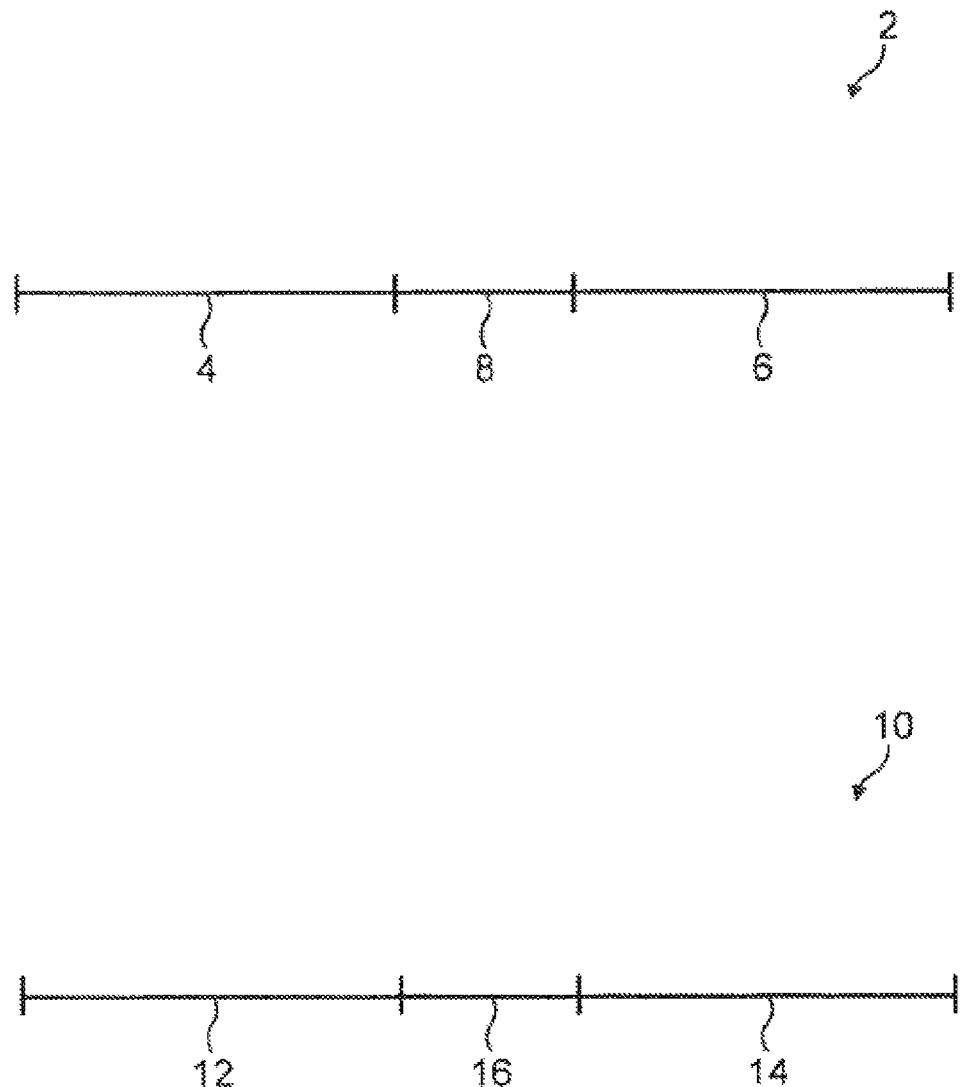
FIG. 1 shows a schematic illustration of first and second synthetic nucleotide oligomers in accordance with an embodiment of the present invention.

Compositions of the present invention comprise a mixture of two different synthetic nucleotide oligomers. Examples are illustrated in FIG. 1. The first synthetic nucleotide oligomer 2 comprises a primer binding sequence 4, a primer binding sequence 6, and an identifier sequence 8 disposed between the primer binding sequences. The second synthetic nucleotide oligomer 10 is similar in structure to the first oligomer and comprises a primer binding sequence 12, a primer binding sequence 14, and an identifier sequence 16 disposed between the primer binding sequences.

The identifier sequences are used to identify the composition. The identifier sequences of the two oligomers are different and together provide a unique code for the composition. The identifier sequences have three to seven bases, preferably 4 to 6 bases. The primer binding sequences are identical or complementary to portions of standard primer sequences used for amplifying the oligomer during analysis.

Figure 2:
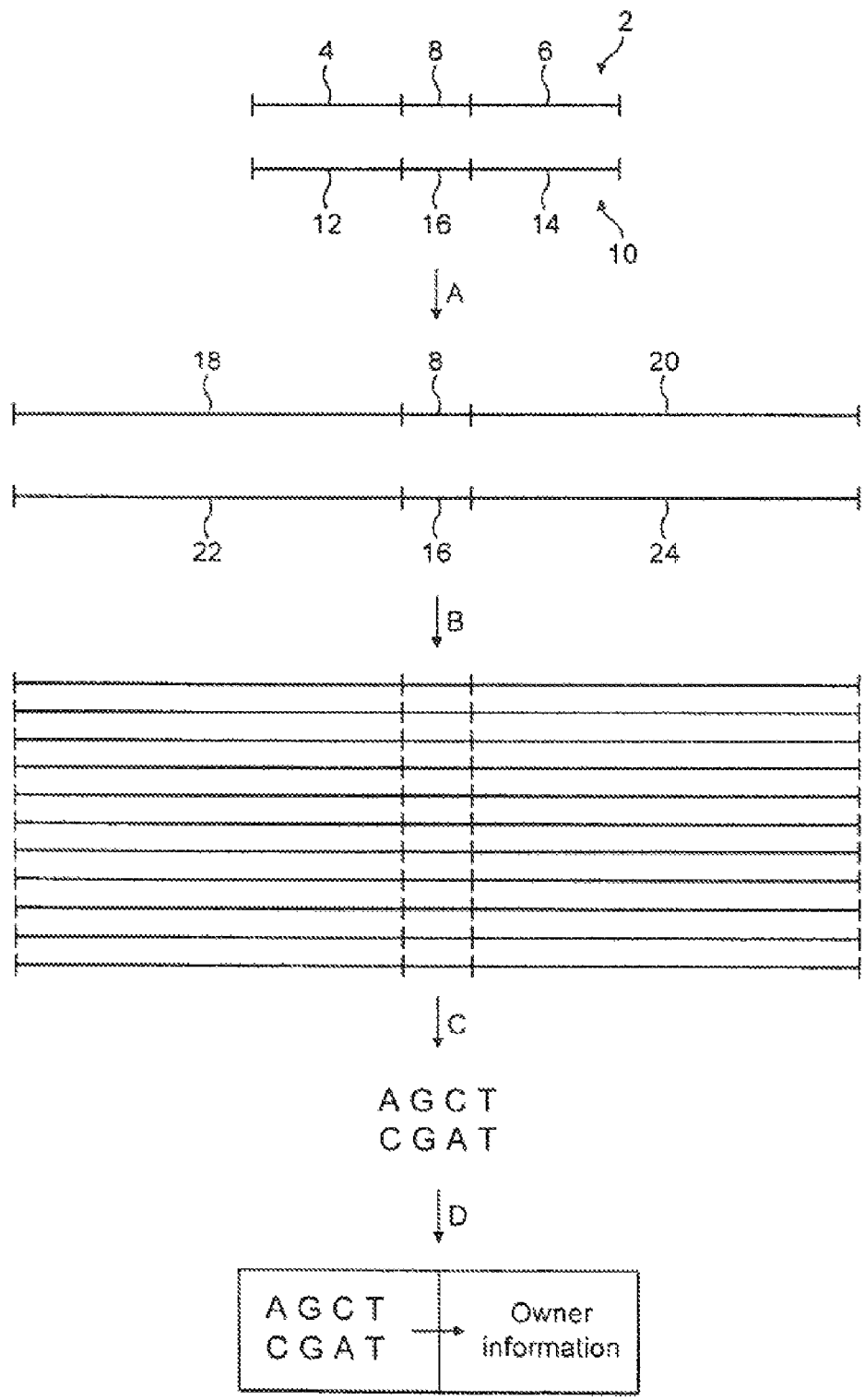
FIG. 2 shows a schematic illustration of a method of determining an owner of a composition in accordance with an embodiment of the present invention.

FIG. 2 shows a method of analyzing a composition comprising a mixture of two different synthetic nucleotide oligomers 2, 10 as described above in relation to FIG. 1.

A sample of the composition is taken and the nucleotide oligomers are isolated. The nucleotide oligomers are then lengthened using primers and then amplified using a polymerase chain reaction. One key feature is that the primers are longer than the primer binding sequences of the nucleotide oligomers 2, 10. Accordingly, the nucleotide oligomers are increased in length as illustrated in Step A of FIG. 2. The extended oligomers retain the same length of identifier sequence 8, 16 but have much longer primer sequences 18, 20, 22, 24 when compared to the original primer binding sequences 4, 6, 12, 14. These extended oligomers are amplified in number using a polymerase chain reaction as illustrated in Step B and then sequenced as illustrated in Step C. The longer oligomers can be sequenced using standard sequencing methods. In contrast, it would be difficult to sequence the shorter oligomers accurately using standard methods. Finally, in Step D a database is used to match the identified sequences with information about the owner of the composition.

Figure 3:
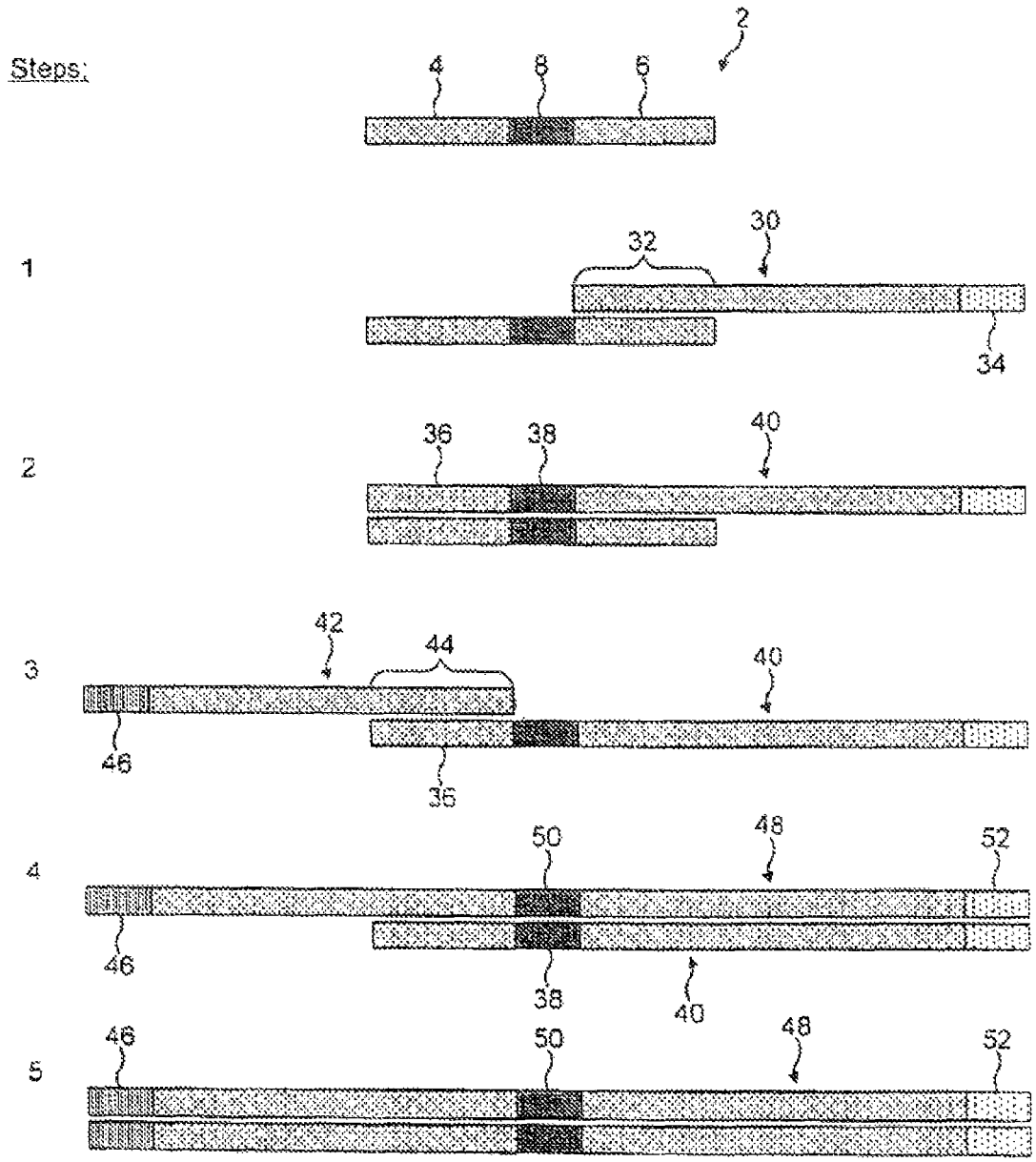
FIG. 3 shows a schematic illustration of a method used to lengthen and amplify one of the nucleotide oligomers in accordance with an embodiment of the present invention.

FIG. 3 shows in more detail a method used to lengthen and amplify one of the nucleotide oligomers. As before, the synthetic nucleotide oligomer 2 comprises a first primer binding sequence 4, a second primer binding sequence 6, and an identifier sequence 8 disposed between the primer binding sequences.

Identification of the DNA security marker is an important part of certain embodiments of the invention, and will now be described in detail.

In Step 1, a PCR primer 30 is bound to the second primer binding sequence 6. The PCR primer 30 has a terminal portion 32 at its 3' end which is complementary to the second primer binding sequence 6 for binding thereto. The PCR primer 30 also has a primer binding site 34 for Sanger sequencing amplification at a position other than the terminal portion 32. In this case, the primer binding site 34 is at the 5' end of the PCR primer 30 and comprises a sequence corresponding to a reverse sequence primer.

In Step 2, the PCR primer sequence 30 is extended using the synthetic nucleotide oligomer 2 as a template so as to form an extended sequence 40 comprising portions 36 and 38 which are complementary to the first primer binding sequence 4 and the identifier sequence 8 of the original synthetic nucleotide oligomer 2.

In Step 3, a second PCR primer 42 is bound to the portion 36 of the extended sequence 40. The second PCR primer 42 has a terminal portion 44 at its 3' end which is complementary to the portion 36 of the extended sequence 40. As the portion 36 is complementary to the first primer binding sequence 6, then the terminal portion 44 of the second primer 42 is identical to the original first primer binding sequence 4.

The second PCR primer 42 also has a primer binding site 46 for Sanger sequencing amplification at a position other than the terminal portion 44. In this case, the primer binding site 46 is at the 5' end of the PCR primer 42 and comprises a sequence corresponding to a forward sequence primer.

In Step 4, the second PCR primer 42 is extended using the extended sequence 40 as a template so as to form a final extended sequence 48 comprising portion 50 which is complementary to portion 38 and thus identical to the identifier sequence 8 of the original synthetic nucleotide oligomer 2. The final extended sequence 48 thus comprises a sequence of a forward sequence primer 46, a sequence of a reverse sequence primer 52, and a sequence 50 identical to the identifier sequence 8 of the original synthetic nucleotide oligomer 2.

In Step 5, the final extended sequence 48 is amplified in number using PCR amplification. The amplification product can then be sequenced using the forward and reverse sequencing primer sites.

The same method steps can be utilized for amplification and sequencing of a second nucleotide oligomer in the composition using a third and fourth PCR primer. In this case, if the first and second PCR primers harbour the same sequencing primer binding sites as the third and fourth PCR primers respectively, the nucleotide oligomers should be amplified and sequenced separately. Alternatively, if the first and second PCR primers harbour different sequencing primer binding sites to the third and fourth PCR primers respectively, the nucleotide oligomers may be amplified in one reaction. However, sequencing analysis should still be performed separately.

The compositions and methods of the present invention allow short nucleotide oligomers to be utilized for uniquely identifying the compositions while enabling standard equipment to be utilized for sequencing the oligomers by extending the length of the oligomers during the initial stages of amplification.

Effective and successful dispersal of the security marker composition is not especially limited. The polyacrylamide spheres may be distributed by many agricultural devices, such as standard broadcasters of fertilizers. The suitable dimensions of this equipment depends on the specific terrain and local conditions.

Figure 4:
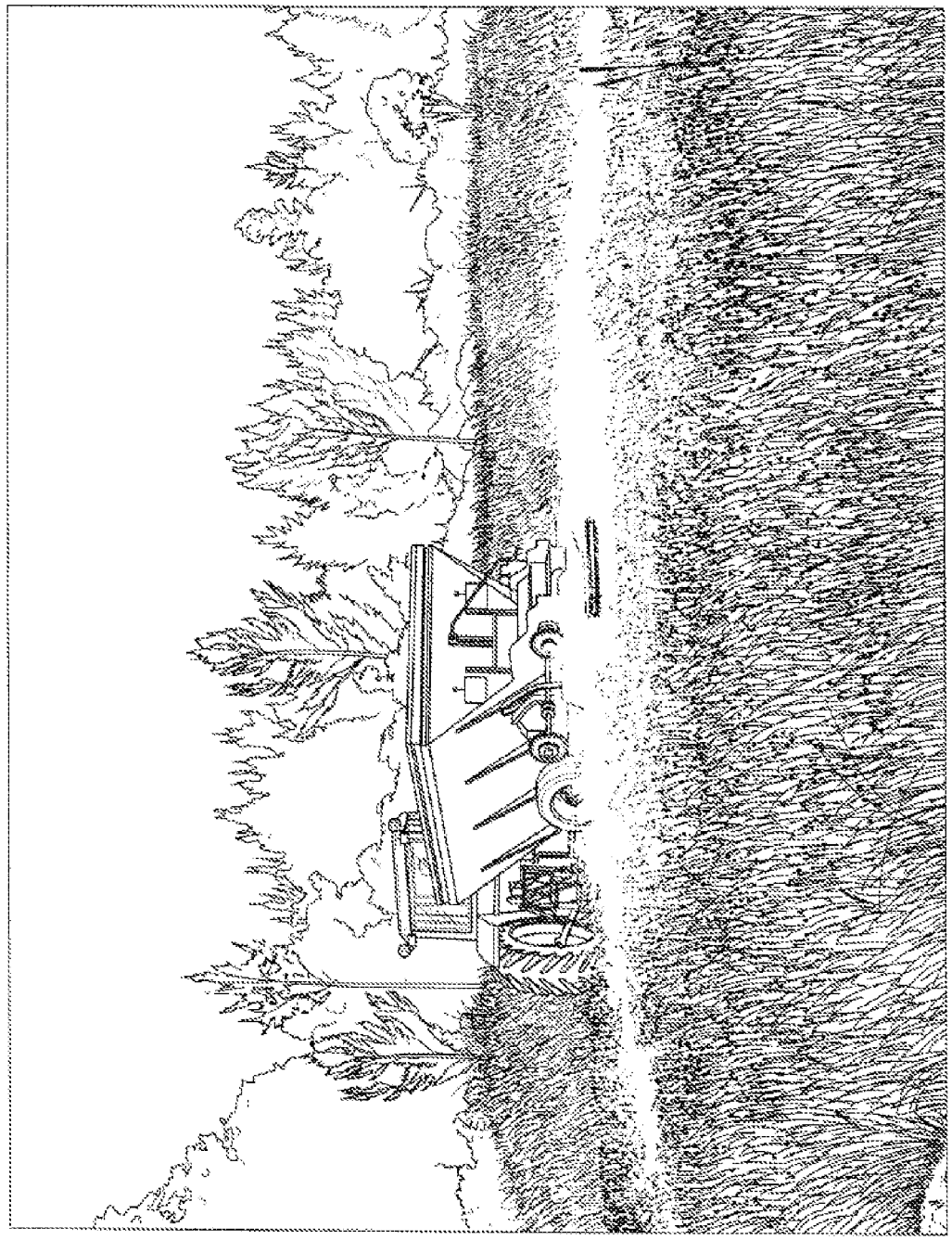
FIG. 4 shows the sticky emulsion being distributed directly on vegetation, in this case in a shrubby area. The method for dispersal is quite straight forward using irrigation equipment such as standard water hoses, sprinklers or even water throwers.
Figure 5:
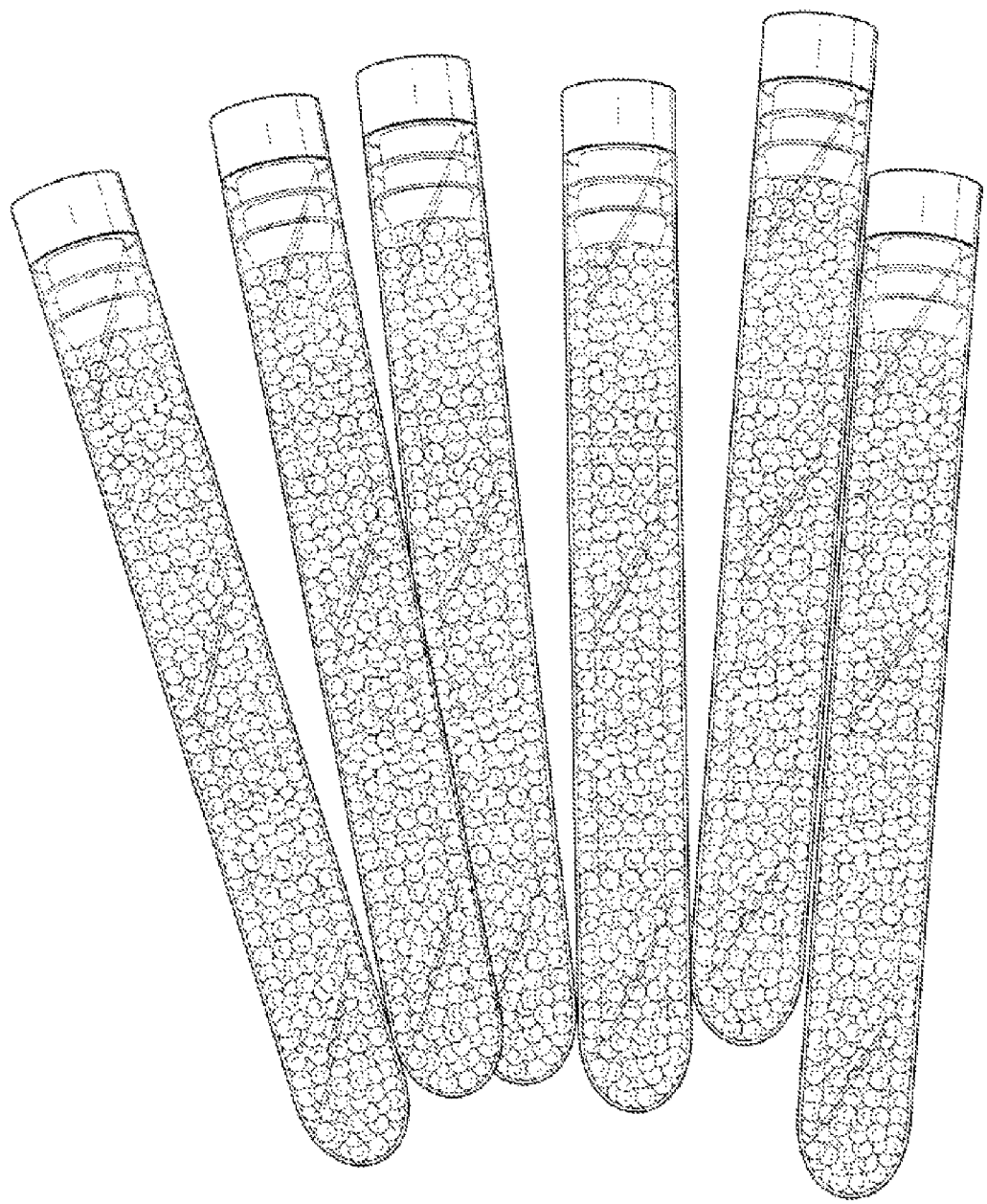
FIG. 5 shows commercially available polyacrylamide balls, which may be employed as a carrier in the present invention.

The sticky emulsion may be distributed directly on the vegetation, preferably in bushy areas (see FIG. 4). The methods for dispersal are quite straightforward, and irrigation equipment such as standard water hoses, sprinklers or even water throwers may be employed.

The sticky threads may be applied manually when used for applications when invisibility is of high priority. For outdoor dispersal it is more suitable to employ hurling equipment or slingshots to distribute the thin threads or fine gardening nets.

While this invention has been particularly shown and described with reference to preferred embodiments, it will be understood to those skilled in the art that various changes in form and detail may be made without departing from the scope of the invention as defined by the appending claims.

The invention claimed is:

1. A security marking composition for marking an area of land, which security marking composition is readily capable of transfer from the land to a person or to a vehicle, which security marking composition comprises:

(a) a carrier comprising a polymer; and (b) a security marker;

wherein the security marker comprises nucleic acid;

wherein the polymer is in the form of threads of polyacrylamide or synthetic spider silk protein, the threads being configured to break and stick to skin or clothing on contact.

2. A security marking composition according to claim 1, wherein the nucleic acid is DNA.

3. A security marking composition according to claim 1, wherein the security marker comprises:

a plurality of identical first synthetic nucleotide oligomers; and a plurality of identical second synthetic nucleotide oligomers which are different to the first synthetic nucleotide oligomers, wherein each of the first synthetic nucleotide oligomers comprises a first primer binding sequence of bases, a first identifier sequence of three to seven bases in length, and a second primer binding sequence of bases, the first identifier sequence being disposed between the first and second primer binding sequences, wherein each of the second synthetic nucleotide oligomers comprises a third primer binding sequence of bases, a second identifier sequence of three to seven bases in length, and a fourth primer binding sequence of bases, the second identifier sequence being disposed between the third and fourth primer binding sequences, wherein the first identifier sequence is different to the second identifier sequence, and wherein information on the owner of the composition is identifiable from the first and second identifier sequences using a database.

4. A composition according to claim 3, wherein the first identifier sequence has a length in the range four to six bases.

5. A composition according to claim 3, wherein the second identifier sequence has a length in the range four to six bases.

6. A composition according to claim 3, wherein the first and second primer binding sequences are different to the third and fourth primer binding sequences.

7. A composition according to claim 3, wherein the first and second primer binding sequences are identical to the third and fourth primer binding sequences.

8. A composition according to claim 3, wherein the first and second primer binding sequences are different.

9. A composition according to claim 3, wherein the third and fourth primer binding sequences are different.

10. A composition according to claim 3, wherein the first, second, third and fourth primer binding sequences each have a length in the range 5 to 40 bases.

11. A composition according to claim 3, wherein each of the first synthetic nucleotide oligomers consists of the first primer binding sequence, the first identifier sequence, and the second primer binding sequence.

12. A composition according to claim 3, wherein each of the second synthetic nucleotide oligomers consists of the third primer binding, the second identifier sequence, and the fourth primer binding sequence.

13. A composition according to claim 1, further comprising one or more of an adhesive, a fluorescent material, a plurality of microdots, a solvent, a propellant, a grease and a gel.

14. A composition according to claim 10, wherein the first, second, third and fourth primer binding sequences each have a length in the range of 10 to 30 bases.

15. A composition according to claim 14, wherein the first, second, third, and fourth primer binding sequences each have a length in the range of 15 to 20 bases.

\* \* \* \* \*